United States Patent [19]
Robinson et al.

[11] Patent Number: 5,269,325
[45] Date of Patent: Dec. 14, 1993

[54] ANALYSIS OF BIOLOGICAL SIGNALS USING DATA FROM ARRAYS OF SENSORS

[75] Inventors: Stephen E. Robinson, San Diego; William C. Black, Jr., Del Mar, both of Calif.

[73] Assignee: Biomagnetic Technologies, Inc., San Diego, Calif.

[21] Appl. No.: 20,175

[22] Filed: Feb. 22, 1993

Related U.S. Application Data

[63] Continuation of Ser. No. 904,891, Jun. 23, 1992, abandoned, which is a continuation of Ser. No. 585,867, Sep. 24, 1990, abandoned, which is a continuation-in-part of Ser. No. 359,640, May 26, 1989, Pat. No. 4,977,896.

[51] Int. Cl.$^5$ .............................................. A61B 5/05
[52] U.S. Cl. ................... 128/653.1; 128/731; 324/248; 324/260
[58] Field of Search ................ 128/653.1, 731; 324/245, 248, 260

[56] References Cited

U.S. PATENT DOCUMENTS

| | | |
|---|---|---|
| 4,309,659 | 1/1982 | Yoshii . |
| 4,731,582 | 3/1988 | Posseme et al. . |
| 4,736,751 | 4/1988 | Gevins et al. . |
| 4,793,355 | 12/1988 | Crum et al. . |
| 4,977,896 | 12/1990 | Robinson et al. ............... 128/653 R |

OTHER PUBLICATIONS

Harald Reucher et al., "Spatial Filtering of Noninvasive Multielectrode EMG: Part I—Introduction to Measuring Technique and Applications" IEEE Trans on Biomedical Eng., vol. BME-34, No. 2 (1987), 98–105.

Harald Reucher et al., "Spatial Filtering of Noninvasive Multielectrode 14 EMG: Part II—Filter Performance in Theory and Modeling", IEEE Trans. on Biomedical Eng., vol. BME-34, No. 2 (1987), 106–113.

P. Nicolar et al., "Spatial filtering in multichannel magnetoencephalography", J. Biomed. Eng. (1989), vol. 11, pp. 79–86.

Robinson, "Theory and Properties of Lead Field Synthesis Analysis" Proc. of Seventh Int. Conf. on Biomagnetism (1989), pp. 599–602.

*Primary Examiner*—Lee S. Cohen
*Assistant Examiner*—K. M. Pfaffle
*Attorney, Agent, or Firm*—Gregory Garmong

[57] ABSTRACT

Signals produced by brain activity are measured by each sensor of an array of magnetic and/or electrical sensors external to but proximate to the head (or other portion of the body) of a subject. The measurements obtained simultaneously from all of the sensors are combined in a manner to permit selective measurement of the electrical activity from a specified location within the body, or alternatively, to permit the location in the body producing a particular type of response to be identified. The instantaneous measurement of each sensor is scaled by a weighting coefficient for that sensor, and the products added over all of the sensors. The weighting coefficients are calculated from the covariance matrix of the measurements made by the array of sensors.

17 Claims, 6 Drawing Sheets

INTENSITY

TIME

ANALYSIS OF BIOLOGICAL SIGNALS USING DATA FROM ARRAYS OF SENSORS

The present invention was made in part under U.S. government contract F33615-89-C-0577. The government may have rights in this invention.

This application is a continuation of application Ser. No. 07/904,891, filed Jun. 23, 1992, now abandoned; which is a continuation of application Ser. No. 07/585,867, filed Sep. 24, 1990, now abandoned; which is a continuation-in-part of application Ser. No. 07/359,640, filed May 26, 1989, now U.S. Pat. No. 4,977,896.

BACKGROUND OF THE INVENTION

This invention relates to the measurement of electromagnetic signals originating in the human body, and, more particularly, to the measurement of magnetic and/or electrical fields originating from brain activity.

The human body produces various kinds of energy that may be used to monitor the status and health of the body. Perhaps the best known of these types of energy is heat. Most healthy persons have a body temperature of about 98.6° F. A measured body temperature that is significantly higher usually indicates the presence of an infection or other deviation from normal good health. A simple medical instrument, the clinical thermometer, has long been available to measure body temperature.

Over 100 years ago, medical researchers learned that the body also produces electrical signals. Doctors today can recognize certain patterns of electrical signals that are indicative of good health, and other patterns that indicate disease or abnormality. The best known types of electrical signals are those from the heart and from the brain, and instruments have been developed that measure such signals. The electrocardiograph measures electrical signals associated with the heart, and the electroencephalograph measures the electrical signals associated with the brain. Such instruments have now become relatively common, and most hospitals have facilities wherein the electrical signals from the bodies of patients can be measured to determine certain types of possible disease or abnormality.

More recently, medical researchers have discovered that the body produces magnetic fields of a type completely different than the other types of energy emitted from the body. The research on correlating magnetic fields with various states of health, disease and abnormality is underway, but sufficient information is available to demonstrate that certain emitted magnetic fields are associated with conditions such as epilepsy. Present medical studies are investigating the nature of the normal and abnormal magnetic fields of the brain, and seeking to correlate those fields with brain functions and patient health.

For example, if it were known that a particular condition, such as epilepsy, were associated with an abnormal magnetic field produced at a particular location in the brain, then it might be possible to detect the abnormality at an early stage, before the condition became acute, and then apply other medical knowledge to treat or surgically remove that precise portion of the brain with minimal side effects on the patient. A selective measurement of brain activity could also permit more precise use of drugs to control the condition. Magnetic studies of the brain therefore offer the potential for understanding and treating some of the most crippling diseases and conditions known.

The biomagnetometer is an instrument that has been developed for measuring magnetic fields produced by the body, particularly the brain and heart. The biomagnetometer is a larger, more complex instrument than the medical instruments mentioned earlier, primarily because the magnetic fields produced by the body are very small and difficult to measure. Typically, at 1 centimeter from the head, the strength of the magnetic field produced by the brain is about 0.000000001 Gauss. By comparison, the strength of the Earth's magnetic field is about 0.5 Gauss, or five hundred million times larger than the strength of the magnetic field of the brain. Most electrical equipment also produces magnetic fields, in many cases much larger than that of the Earth's field. It is apparent that, unless special precautions are taken, it is not possible to make magnetic measurements of the human body because the external influences such as the Earth's magnetism and nearby apparatus can completely overwhelm and mask the magnetic fields from the body.

The biomagnetometer includes a very sensitive sensor for magnetic signals. The currently most widely used sensor is a Superconducting QUantum Interference Device or SQUID, which is sufficiently sensitive to detect magnetic signals produced by the brain. (See, for example, U.S. Pat. Nos. 4,386,361 and 4,403,189, whose disclosures are incorporated by reference, for descriptions of two types of SQUIDs.) This detector and its associated equipment require special operating conditions such as a cryogenic dewar, and cannot be placed into the body or attached directly to the surface of the body.

The present biomagnetometer therefore provides a chair or table for the patient, and a structure which places the detector in proximity with the head of the patient, as about 1-2 centimeters away. Special electronics is provided to filter out external effects such as the Earth's magnetic field and the magnetic fields of nearby electrical instruments. (For a description of such a device, see U.S. Pat. Nos. 3,980,076 and 4,079,730, whose disclosures are herein incorporated by reference.) The patient and detector can also be placed into a magnetically quiet enclosure that shields the patient and the detector from the external magnetic fields. (For a description of such an enclosure, see U.S. Pat. No. 3,557,777, whose disclosure is herein incorporated by reference.) With these special precautions, medical researchers and doctors can now make accurate, reliable measurements of the magnetic fields produced by the brain, and are studying the relationship of these fields with diseases and abnormalities.

It is well established that certain physically identifiable locations in the brain are responsible for specific types of activities and functions. It is therefore important to correlate the measured biomagnetic field with the particular location in the brain which produces the field. Such a correlation is important to understanding the mechanism by which disease and disorder arise, and also to the treatment of the problem.

Correlating the spontaneous measurement taken by an external array of magnetic or electrical sensors with brain activity at a specific location within the brain is difficult, primarily because other areas of the brain continue to function and produce their own magnetic and electrical fields, even as a measurement is being taken with the intent of measuring activity at a specified location, and because the measurement sensors and instrumentation produce noise that may be of the same magnitude as the signals to be measured. It is not easily determined whether a particular signal measured externally originates at the selected location, other locations, or jointly at the selected location and other locations, or in fact is a manifestation of instrument noise. At the present time, there is a good deal of reliance on averaging multiple occurrences of magnetic and/or electric signals synchronously with external events such as a stimulus, to isolate the origin of particular magnetic signals.

Moreover, it is difficult to develop data from spontaneous brain activity, having a high signal to noise ratio, that can reliably be said to originate at a selected location in the brain. Having such a capability would be extremely useful, because it would permit studies of neurological disorders associated with epilepsy, stroke, and head injury, for example, and even direct physiological studies of some of the most basic phenomena of life, such as attention and boredom, mental disorders, language comprehension and expression, and response to external stimuli.

An important step in correlating external measurements with the specific locations of internal events is disclosed in U.S. Pat. No. 4,793,355, whose disclosure is incorporated by reference, and which provides a methodology for automatically tracking the position of the sensors in respect to the position of the head of the patient. When used in conjunction with the known spatial sensitivity profile of the detector and either an external stimulus or synchronization with voluntary activity, this approach gives important information about the internal origin of the externally measured signal. This technology, by itself, is limited in its resolution of location and nature of the source, because of various types of noise and the continued operation of other brain functions as measurements are taken. It is also limited in its ability to investigate spontaneous, non-evoked brain activity.

There is therefore a need for an improved approach for measuring biomagnetic fields and correlating those fields with their source location within the brain. Preferably, such an approach would permit data to be simultaneously obtained for a number of different signals produced from sensors in a number of different locations, to permit correlation of all signal information. The approach also must achieve a high signal to noise ratio that permits the signal of interest to be discerned and isolated relative to other brain signals, external noise, and instrument noise. The present invention fulfills this need, and further provides related advantages.

SUMMARY OF THE INVENTION

The present invention provides an approach for analyzing electromagnetic signals, such as magnetic and electrical fields, produced by the body. It permits selection of the location within the body from which the signals are to be examined, and an excellent characterization of the signals themselves with an optimized signal to noise ratio. The approach can be practiced with existing hardware, or can utilize apparatus that is specially designed for the purpose.

The present invention further provides an approach for utilizing multiple electromagnetic sensors of an array in combination to obtain better information about the functioning of an electromagnetic source within the body, than could be obtained from the uncombined data of the individual sensors of the array. It provides an approach for mathematically combining the outputs of the sensors of the array in a manner that effectively defines a virtual sensor which is optimized for measuring a particular location within the body, based upon the characteristics of the sensors, the sources, and the body, and their relative locations. The outputs of the individual sensors are weighted and added together to define the virtual sensor output, and different virtual sensors can be defined from a fixed sensor array. The results do not depend upon the applicability of a particular model of the brain or the sources therein, but instead are derived mathematically from the measurements themselves according to the events that occur during the measurement period.

In accordance with the invention, a process for sensing and evaluating signals emanating from the brain of a subject comprises the steps of providing an array of field sensors disposed external to a head of a subject at known locations; measuring a signal strength detected by each of said sensors; multiplying the signal strength measured by each of said sensors times a weighting coefficient for that sensor to determine a virtual sensor contribution for each of said sensors, said weighting coefficient for each of said sensors being determined at least in part by the signal strengths detected by said array of sensors; and adding together the virtual sensor contribution of each of said sensors, to define a virtual sensor signal.

Alternatively stated, a process for sensing and evaluating signals emanating from a body of a subject comprises the steps of measuring a signal strength detected by each sensor of an array of electromagnetic sensors placed proximately to a body of a subject; and calculating a virtual sensor signal for the array, as a sum, over all of said sensors, of a product of a weighting coefficient for each sensor times the signal measured for that sensor, the weighting coefficients being determined from measurements of the signal strengths of said array.

In yet another form, a process for sensing and evaluating electromagnetic signals emanating from a body of a subject comprises the steps of providing an array of electromagnetic field sensors disposed external to a body of a subject at known locations; measuring a signal for each of said sensors; determining a weighting coefficient applicable to each of said sensors from the measurements made in said step of measuring; multiplying the signal strength measured by each of said sensors times the calculated weighting coefficient for that sensor to determine a virtual sensor contribution for each of said sensors; and adding together said virtual sensor contribution of each of said sensors, to define a virtual sensor signal.

The present invention utilizes the combined response data gathered by each one of an array of sensors external to the body. The sensors can be sensitive to magnetic fields or electrical fields, and the term "electromagnetic" is used herein as a generic descriptor for signals, detectors, or the like to encompass both types of phenomena. The combined data can be treated to attain an optimized characterization of the signal produced from a selected location in the brain or other source. By combining the same response data of the sensors in different ways, simultaneous occurrences in different parts of the body can be understood by themselves and in relation to each other. The present approach can be used to measure any portion of the body from which electromagnetic signals originate, including but not limited to the brain, the heart, muscle tissue, nerves, etc.

To calculate the virtual sensor signal corresponding to an electromagnetic field generated at a selected location in the brain, the signal strength measured by each sensor at a point in time is multiplied by a weighting coefficient determined for that sensor, and then all the products of signal strength and weighting coefficient are added together. The weighting coefficient is calculated from the actual measurements of the sensors, together with the relative positions and orientation of the sensors and the selected location in the body, and the spatial sensitivity of the sensor, known as its lead field. From this last component comes the term used to describe this type of analysis, "lead field synthesis" ("LFS").

One desirable feature of this approach is that the nature of the virtual sensor, attained from the weighted combination of the signals of the individual physical sensors, can be changed to tune the response of the virtual sensor to different locations, using the same measured data. Thus, with a first set of weighting coefficients, the virtual sensor is directed to sample a first location in the body, and with a second set of weighting coefficients, the virtual sensor is directed to sample a second location in the body, in both cases using one set of actual measurement data from the physical array of sensors.

Another desirable feature is that the virtual sensor may be tuned for an optimal signal to noise ratio for a particular location, again through the mathematical model that provides the weighting coefficients. The signal to noise ratio is improved by making the virtual sensor less sensitive to brain activity in regions that are not of interest, or by reducing the effective instrument noise, including unwanted environmental signals. This capability permits the virtual sensor to utilize sophisticated signal acquisition and processing theories already known but never applied to the understanding of the body. The virtual sensor provides a means of combining data from both magnetic and electrical field sensors into a virtual sensor whose measurement units are source strength. This combination renders the measurement of activity independent of the type of sensor or its location.

The virtual sensor signal can be interpreted as the amount of the signal strength measured by all sensors simultaneously which could have originated at a specified source within the brain, to which the virtual sensor is directed.

The approach of the invention may be used with existing biomagnetometers such as that disclosed in U.S. Pat. No. 4,793,355, and available commercially from Biomagnetic Technologies, Inc., San Diego, Calif. These biomagnetometers provide a large number of SQUID-type sensors in an array placed at various positions around the head of the subject under study. The response signal of each sensor is recorded separately, and combined using the approach just described to calculate a virtual sensor response. However, it is possible that other arrays of sensors may be devised that are optimally placed for utilization of the lead field synthesis methodology. In particular, it is expected that larger arrays of electromagnetic sensors, measuring magnetic and electrical signals, will provide even more precise information about the magnitude of signals originating at a particular location within the body.

Other features and advantages of the present invention will be apparent from the following more detailed description of the preferred embodiment, taken in conjunction with the accompanying drawings, which illustrate, by way of example, the principles of the invention.

DETAILED DESCRIPTION OF THE PREFERRED EMBODIMENT

The approach of the present invention can be used in conjunction with measurements of magnetic and electrical signals from any and all parts of the body. Signals produced from the brain are of great interest, and the preferred embodiment is directed toward this application. The methodology, however, is more generally applicable.

Figure 1:
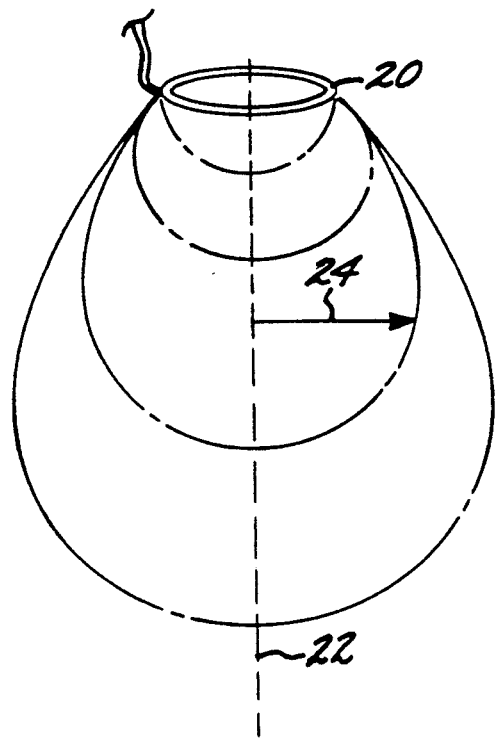
FIG. 1 is a schematic representation of the sensitivity of a single-loop magnetic sensor.

Sensors used to detect magnetic or electrical signals generated in the brain, like all such sensors, are directional in nature and have a sensitivity to signals that depends on the physical position of the sensor relative to the location whereat the signal originates, the orientation of the sensor, and the nature of the source of the signal. Generally, as illustrated in FIG. 1 for a single loop magnetic field sensor 20, the further the origin of the signal from the sensor, the less sensitive the sensor is to the signal. Sensitivity, as represented by the curves of the figure extending below the sensor 20, decreases with increasing axial distance along the axis 22 of the loop, and also with radial distance 24 from the axis 22. The pattern of FIG. 1 is illustrative of such sensitivity variations.

Another aspect of the design of sensors is that the larger the loop of the sensor, the more sensitive it should be to measuring small uniform magnetic fields, because more magnetic flux lines can pass through the loop. However, the placement of the sensor also influences its sensitivity to particular signals.

If one knows beforehand the location of the origin and the orientation of a specific signal to be measured, an optimal design and placement for the sensor used to measure the signal can be selected. However, such is not possible for a general-purpose approach, nor is it possible where signals from many locations are to be measured simultaneously or nearly simultaneously.

Figure 2:
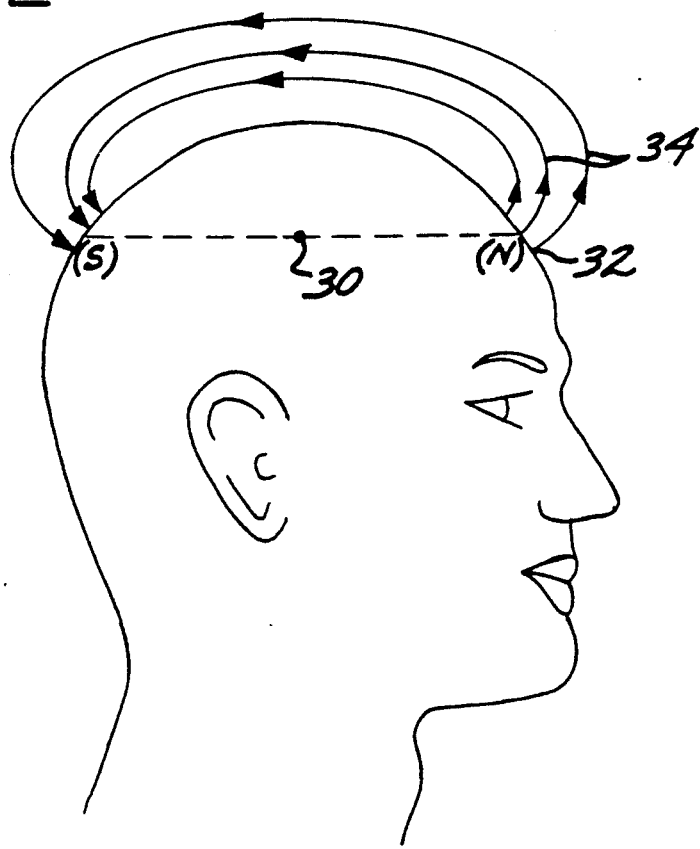
FIG. 2 is a schematic diagram of the magnetic field of a source in the brain.

The following example illustrates the principles of sensor selection for a known source in the brain. The brain generates magnetic signals as a result of electrical currents that originate within the brain. FIG. 2 illustrates the magnetic field produced by a source 30 within the head 32 of the person. The field originating at source 30 is produced by a neural current passing in the direction perpendicular to the page, along a group of neurons located at source 30. Magnetic field lines 34 emerge from the skull to the external environment, where a sensor may be located.

Figure 3:
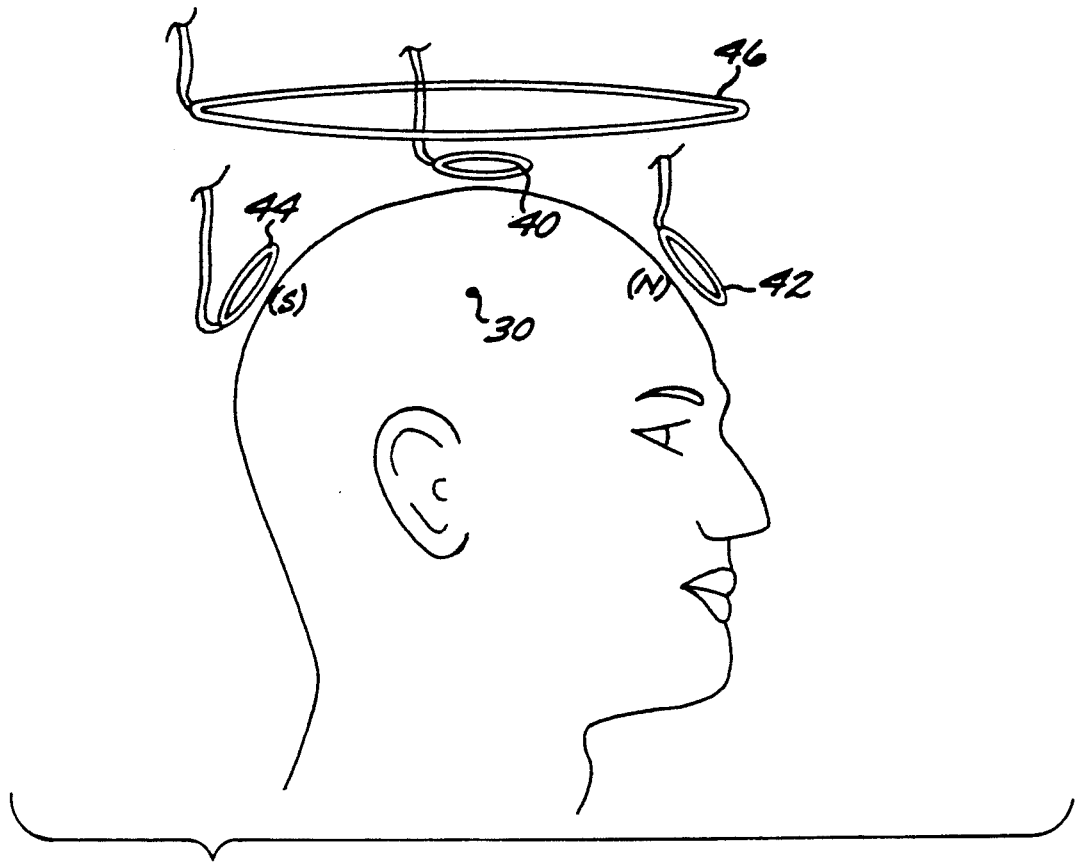
FIG. 3 is a schematic diagram of the placement of sensors to measure the magnetic field of a source in the brain.

FIG. 3 shows the same source 30, but with some external loop sensors positioned to measure the magnetic field. A sensor 40, positioned directly over the current source 30, registers no signal because no magnetic field lines 34 (omitted from FIG. 3, but the same as in FIG. 2) pass through the loop of the sensor 40. A sensor 42 is located above the N pole, and registers a maximum positive signal. A sensor 44 is located above the S pole, and registers a maximum negative signal. A much larger sensor 46, symmetrically located with respect to the N pole and the S pole, although more sensitive to uniform magnetic fields, registers no signal because the net flux through the loop of the sensor is zero.

Figure 4:
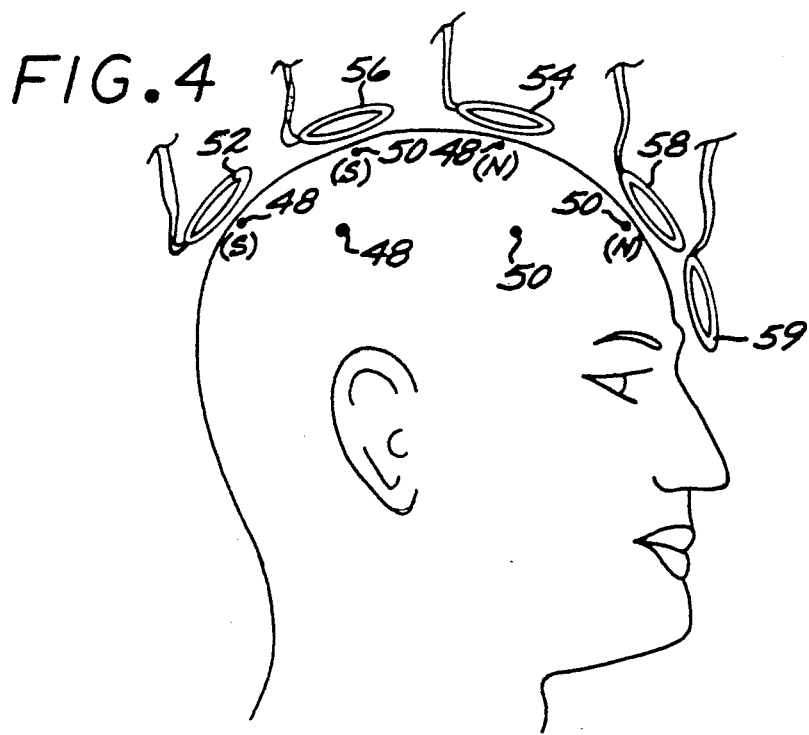
FIG. 4 is a schematic diagram of the placement of sensors to measure the magnetic field of different sources in the brain.

The actual problem faced in making measurements of signals originating in the brain is that, unlike the example illustrated in FIGS. 2 and 3, the location and orientation of the signal source is not known. FIG. 4 illustrates the nature of the sensing problem where there are two sources, and also the origin of the present analytical approach. Where there are two sources 48 and 50, sensors 52 and 54 placed over the 48N and 48S poles for source 48 will be most sensitive to that source, but will also detect some signal due to the other source 50. Likewise, sensors 56 and 58 placed over the 50N and 50S poles for source 50 will be most sensitive to the source 50, but will also detect some signal due to the other source 48. A sensor 59 may be placed so that it does not provide much information about either of the sources 48 and 50.

Thus, if there were a way to utilize the readings of sensors 56, 58, and 59 so as to render the measurements of sensors 52 and 54 insensitive to source 50, an optimal measurement of source 48 could be obtained. This result can be accomplished by subtracting the interfering signal arising from source 50, as best detected by sensors 56 and 58, from the signals detected by sensors 52 and 54, which respond maximally to the desired source 48. Thus, by knowing the proportions and sign with which to combine the signals from all sensors, an optimal measurement can be obtained for a specified source, and interference from unwanted sources can be suppressed. A similar principle holds for obtaining an optimal measurement from source 50 by utilizing the sensors 56 and 58, which convey information primarily about source 50, and sensors 52, 54, and 59, which convey information primarily from the source 48.

Even for the relatively simple example of FIG. 4, the problem of sensing becomes more difficult if none of the sensors are located at the optimal positions for measuring the field of a selected source location and orientation. If none of the sensors of the array 52, 54, 56, 58, and 59 are optimally placed to measure a selected source, then some method must be chosen to utilize the data from some or all of the sensors in order to measure that source.

In principle, the sensitivity of the array of sensors 52, 54, 56, 58, and 59 can be adjusted or "tuned" to be optimally sensitive to signals originating from sources in the brain of particular locations and orientations. The approach for achieving such tuning is apparent from the very simple example of FIG. 4, where the locations and orientations of the sources 48 and 50 were specified. The approach is not apparent for the more complex case of millions of sources of signals in the brain having locations and orientations that are not known beforehand, where a relatively small number of sensors are present in the array of sensors, and where there is no prior knowledge that the sensors are optimally placed for measuring a signal.

The present invention provides a technique for utilizing the data produced by an array of sensors to synthesize a "virtual" sensor that is optimally sensitive to a selected source within the body.

Considering both the spatial sensitivity of the sensor, as illustrated in FIG. 1, and the geometric realities of sensor placement, as illustrated in FIGS. 2–4, it is apparent that the needs of a general measurement approach result in some apparently contradictory hardware requirements. Small diameter sensors are desirable to achieve good resolution of signals from shallow locations close to the skull, while large diameter sensors are desirable to achieve measurement of deep sources. Sensors should somehow be effectively capable of being repositioned to measure some sources, while remaining stationary to measure those sources for which they are optimally positioned.

Figure 5:
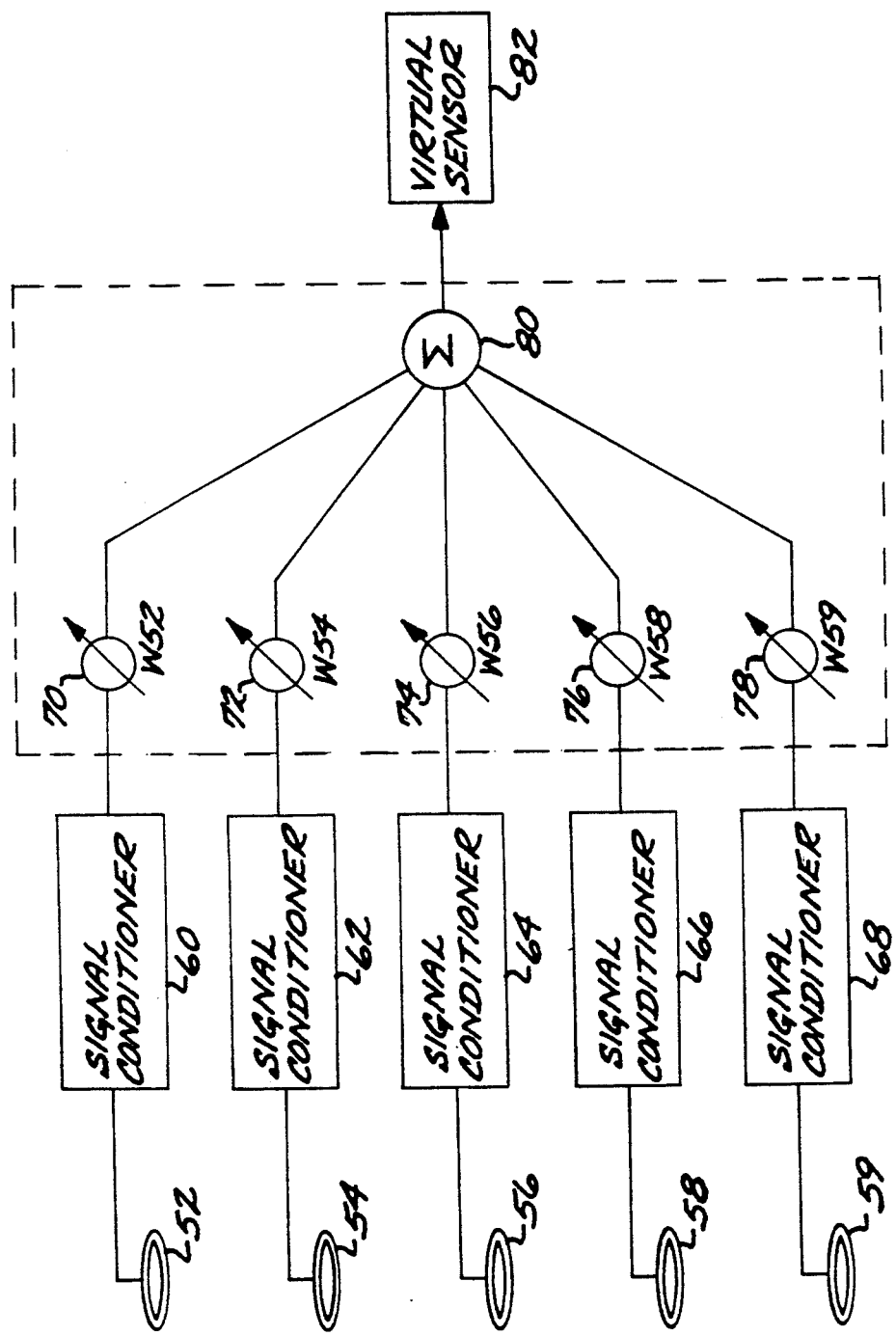
FIG. 5 is a schematic diagram of the manner of combining the measurements of an array of sensors.

The present approach permits these apparently contradictory requirements to be met by utilizing all of the data from the multiple sensors to arrive at a single scalar number that is representative of the magnetic signal produced from a selected location, without physically moving or replacing any of the sensors. As illustrated in FIG. 5, each response signal strength measured by a sensor such as sensors 52, 54, 56, 58, and 59 is first detected and conditioned by filtering and amplifying as necessary, in a signal conditioner depicted as element 60, 62, 64, 66, and 68, respectively. Such detection and signal conditioning apparatus is well known in the art, and is used for existing sensors.

The conditioned signal for each sensor is then multiplied by its own particular signed weighting coefficient, here illustrated as the weighting coefficients $w_{52}$, $w_{54}$, $w_{56}$, $w_{58}$, and $w_{59}$, respectively, in individual multiplying operations 70, 72, 74, 76, and 78. The sign (plus or minus) of the weighting coefficient is taken into account in performing the multiplying operation. A negative weighting coefficient results in a scaled product of polarity opposite to that of the original signal. Each of the resulting arithmetic products is supplied to an adder 80, which adds them together for the five sensors 52, 54, 56, 58, and 59. The resulting sum is supplied as a scalar signal termed a virtual sensor 82. In the preferred approach, the signals from the signal conditioners 60, 62, 64, 66, and 68 are digitized and supplied to a digital computer, which performs the multiplier functions 70, 72, 74, 76, and 78, and the adding function 80, in digital format. (The preceding example dealt with only five sensors, but the present invention is not so limited. Preferably, much larger arrays of sensors are used to improve resolution of sources, and the present approach has been tested with data taken from an array of 37 sensors.)

The effect of the summing of weighted signals approach may be understood with reference to FIG. 4. With regard to the measurement of the magnetic field emanating from the source 48, the sensor 59 would gather almost no useful information, and in fact measure mostly brain noise relative to the source 48. The weighting coefficients of sensor 59 would be a small value. The sensors 52 and 54, on the other hand, gather a great deal of information about the source 48, and their weighting coefficients would be large and of opposite sign. The sensors 56 and 58 present the most difficult aspect of the analysis, since they provide some useful information about the source 48, but also a good deal of brain noise resulting from other sources, such as the source 50 (which must be considered noise when one attempts to study the signal produced by the source 48). The weighting coefficients of the sensors 56 and 58 would be of opposite sign to that of the sensors 52 and 54.

Using the same information gathered from sensors 52, 54, 56, 58, and 59, optimized information about the source 50 can be synthesized. Once again, the weighting coefficient for the sensor 59 would be small, because it contributes little useful information to analyzing the source 50. However, in this case the weighting coefficients for the sources 56 and 58 would be large, since they are optimally placed for measuring source 50. The weighting coefficients for the sources 52 and 54 would be of opposite sign, because they gather some useful information but also reflect brain noise from source 48 (which in this case is considered noise with respect to the source 50 of interest) and other sources.

The information gathered by the array of sensors 52, 54, 56, 58, and 59 may be combined with yet other weighting coefficients to measure other sources not illustrated in FIG. 4. Although in the hypothesized examples of FIG. 4, the sensor 59 contributed little of use in measuring either source 48 or 50, for other sources in different locations the sensor 59 may become the most highly weighted sensor and some or all of the sensors 52, 54, 56, and 58 may have lower weights and different signs.

Only one set of actual physical measurements using the sensors 52, 54, 56, 58, and 59 is made to yield information about the sources 48 and 50. The analytical approach permits those measurements to be combined in several ways, by using different weighting coefficients, to obtain the information about the individual sources. It is therefore possible, when the computer is used for the computations, to make one measurement using the sensors, store the measured values in the computer, and then perform a large number of computations using that measured and stored experimental data to deduce information about the magnetic signals produced by different sources at a single instant in time. Subsequent experimental results for the sensors are similarly stored and processed, permitting an understanding of the operation of each of the sources over time, both as to their individual operation and as to any interactions that may occur between sources.

The examples just presented illustrated the philosophical basis of lead field synthesis. However, they are purposely made to be not complex to illustrate the principles and possibilities of the approach. The vector nature of the sources 48 and 50, the type of source operating, and the magnetic permeability and electrical conductivity of the air, skull, and brain matter have not been discussed. Nor have the exact sensor locations and orientations, and the detailed geometry of the brain been incorporated into this qualitative description.

The more general implementation of lead field synthesis requires a mathematical study of the interaction of electromagnetic sources and sensors. The response of a magnetic sensor to a current source in the brain is directly proportional to the current I induced in the sensor coil, $$I = k \int \vec{G}(\vec{r}) \cdot \vec{H}(\vec{r}) dV$$

where $\vec{G}(\vec{r})$ and $\vec{H}(\vec{r})$ are the sensor lead field and the magnetic field generated by the source current at position $\vec{r}$. $\vec{G}(\vec{r})$ is a characteristic of the sensor, and $\vec{H}(\vec{r})$ is calculated form the source and media properties, as will be described subsequently.

If the sensor output of an array of sensors is represented as a vector $\vec{S}$ and the weight to be accorded each sensor is represented by a vector $\vec{w}$ of equal dimension, the scalar output signal V is the dot product of the weight and sensor output vectors:

$$V = \vec{w} \cdot \vec{S}$$

Thus, the lead field of a virtual sensor defined by the summation of the weighted outputs of an array of sensors is $$G_v = \sum_i w_i G_i$$

For an array of M sensors and a model, $\Omega$, of all potential sources of brain signal, including a target source, the Gram matrix is computed as $$\Gamma_{ij} = \int_\Omega \vec{G}_i \vec{G}_j d\Omega$$

where $(i, j = 1, \ldots, M)$ and $G_i$ is the Green's function for the response of the ith detector at the integration point in source space. By specifying the Green's functions for the desired "target" source, $\vec{G}_T$, a set of coefficients $\vec{W}$ can be calculated as $$\vec{W} = \Gamma_{ij}^{-1} \vec{G}_T.$$

One approach to solving this problem is set forth in the allowed parent application, Ser. No. 07/359,640, whose disclosure is incorporated by reference. This approach necessarily requires the development of a model of the brain, which in some instances may be difficult.

The more potential sources relative to the number of sensors, the more difficult it is to distinguish a single signal, leading to a "blurriness" of the solution. However, the scope of the problem may be reduced, leading to a more precise solution, by limiting the number of sources to those actually operating during any particular measurement period of time.

A covariance matrix $C_{ij}$ may be written as $$C_{ij} = \frac{1}{T} \int_T (X_i(t) - \overline{X}_i)(X_j(t) - \overline{X}_j) dt$$

where $X_i$ is the signal received by a sensor during a period of time dt and $\overline{X}_i$ is the mean signal of that sensor during integration time T. Other than a scale factor, the covariance matrix is a "local" (in a temporal sense) estimator of the Gram matrix. The two matrices contain similar information, the Gram matrix from the source point of view and the covariance matrix from the sensor point of view. They each represent the interrelationship of the responses or lead fields of each of the sensors to each of the sources.

The scale factor relating the covariance matrix to the Gram matrix is calculated by requiring that the transfer function at the target location must be unity. That is, $\vec{W} \cdot \vec{G}_T = 1$. The unscaled lead field synthesis coefficients, alpha, are:

$$\overline{alpha} = [C_{ij}]^{-1} [\vec{G}_T].$$

Using the definition of transfer function, the scale factor relating the covariance matrix to the Gram matrix is $\vec{G}_T \overline{alpha}$.

The scaled lead field synthesis coefficients are therefore $$\vec{W} = \overline{alpha} / \vec{G}_T \overline{alpha}$$

or alternatively stated $$\vec{W} = [C_{ij}]^{-1} [\vec{G}_T] / [\vec{G}_T] \cdot [C_{ij}]^{-1} [\vec{G}_T].$$

This result is important, because it means that a statistical measure of the body field signal, the covariance matrix $C_{ij}$, can be combined with generalized inverse theory to compute optimal brain noise reduction coefficients $\vec{W}$.

This approach has been assessed with actual test results for a 37-channel biomagnetometer, using an approach like that just discussed but with 37 sensors rather than five. The relative physical locations of the sensors with respect to sites on the surface of the head and inside the brain matter may be determined in real time, simultaneous with the field measurements, in the manner illustrated in U.S. Pat. No. 4,793,355 or other acceptable manner. In general, a series of vectors defines points and locations with respect to each other, and the structure disclosed in the '355 patent permits such vector location information to be determined and stored by measurements in real time. The geometry of the outer surface of the head can also be measured and recorded in the manner disclosed in the '355 patent.

Figure 6:
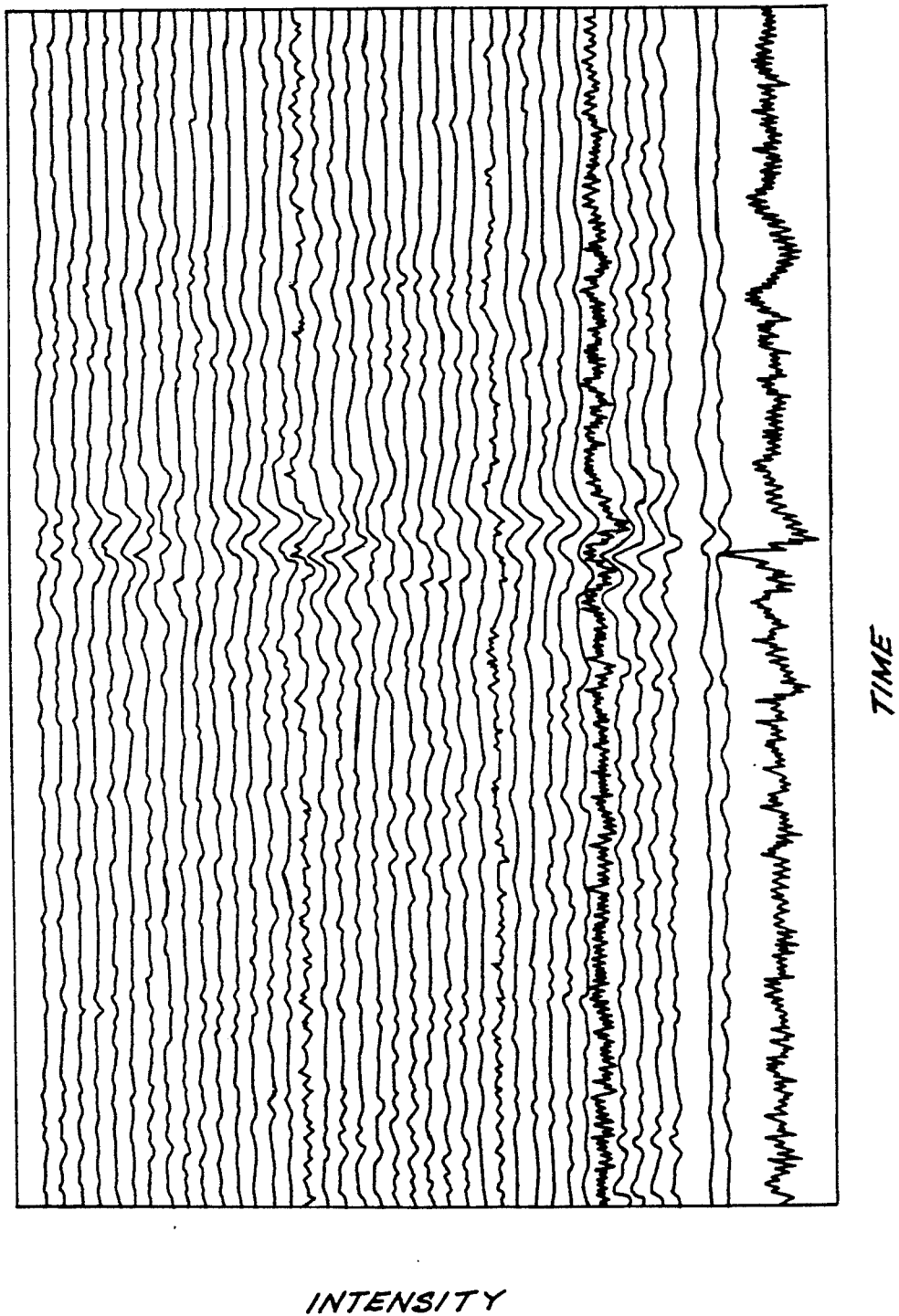
FIG. 6 is a graph of signal intensity as a function of time for 37 channels of biomagnetic data, 2 channels of EEG data, and the result of a spatial filtering calculation.
Figure 7:
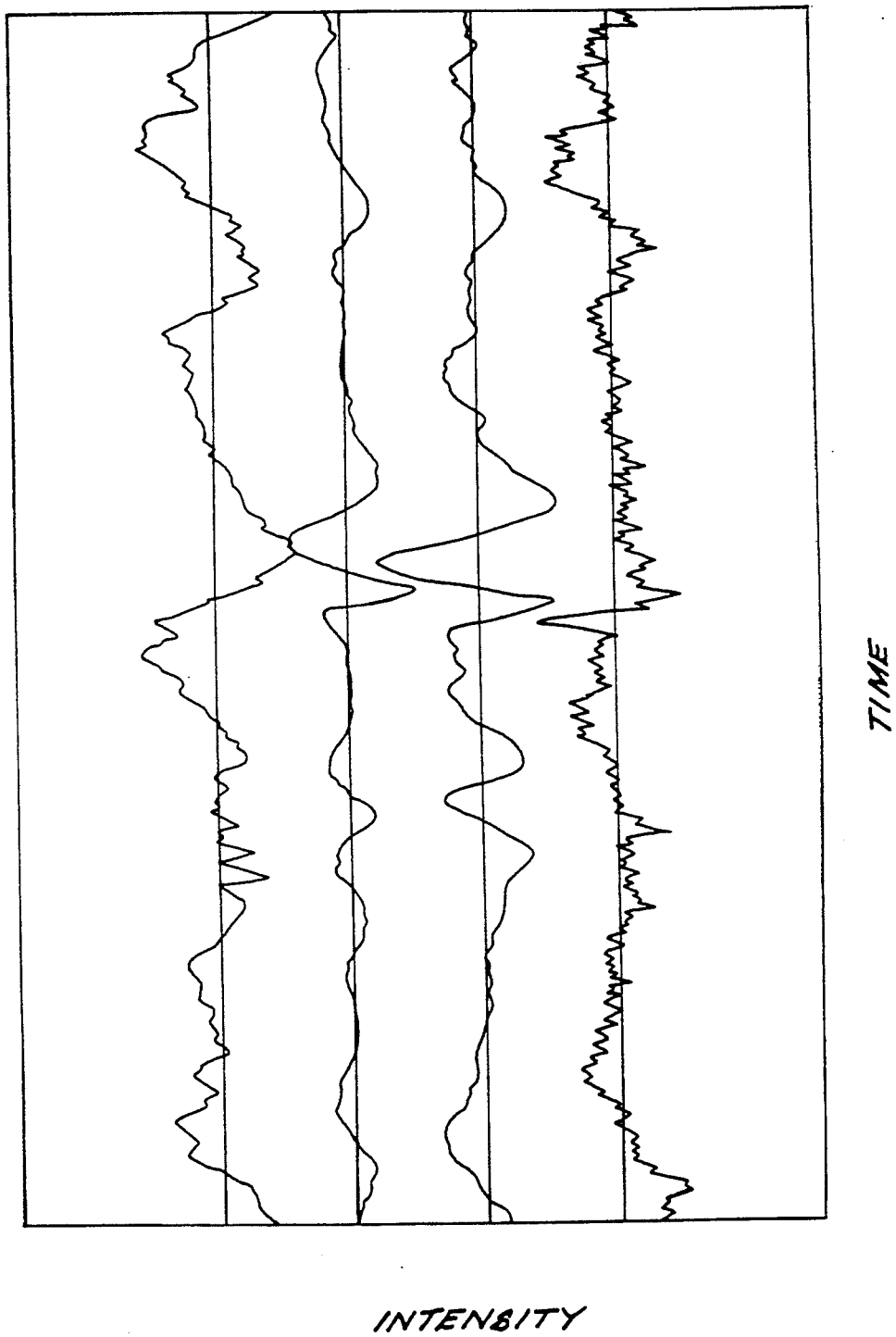
FIG. 7 is a graph of signal intensity as a function of time for 1 channel of biomagnetic data, 2 channels of EEG data, and the result of a spatial filtering calculation.
Figure 8:
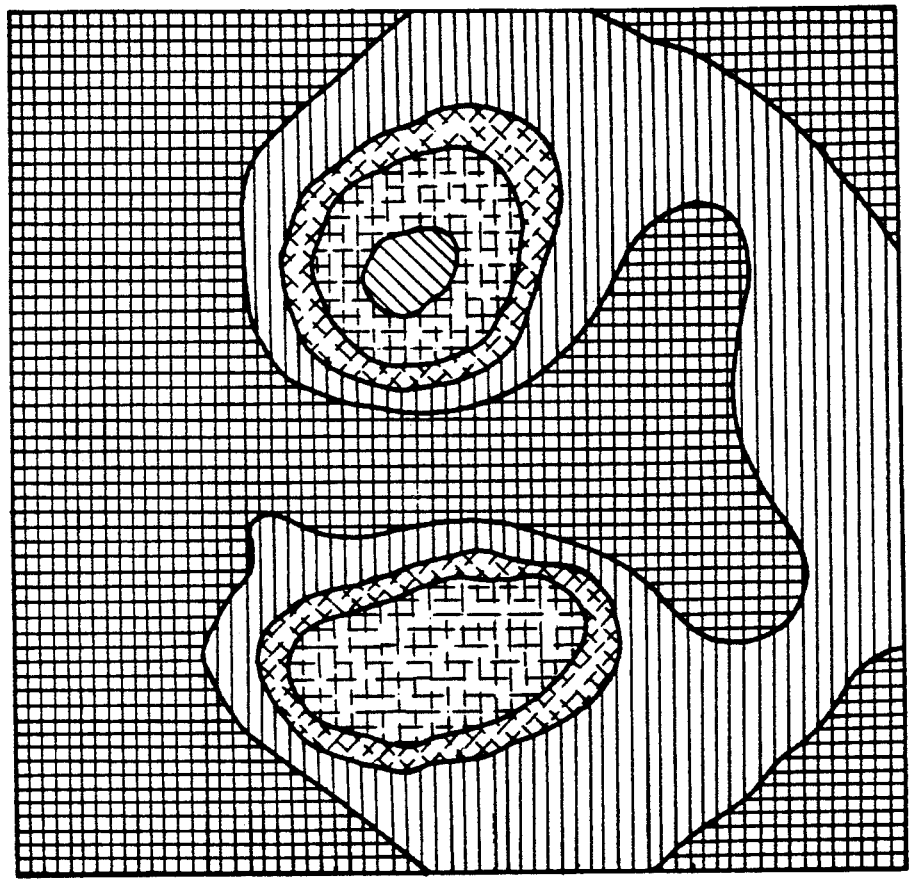
FIG. 8 is a plot of image intensity as a function of position within the brain at a moment in time during an epileptic episode.

FIGS. 6-8 illustrate some of the results of this assessment. FIG. 6 presents the signal magnitude as a function of time for the 37 channels of biomagnetic data (the top 37 lines), 2 channels of EEG data, and the spatially filtered analysis of the information (bottom line) for a specific selected location within the brain. In the central portion of the figure, the occurrence of an event can be discerned from some of the channels, but its magnitude and time cannot readily be determined. The spatially filtered result clearly shows the location in time of the event as a major peak. Spatial filtering thus is useful in ascertaining the fact of an event whose presence is difficult to determine otherwise in the measured data.

FIG. 7 also illustrates signal magnitude as a function of time, in this case on expanded scales and presenting only the clearest of the biomagnetic signal channels, channel 35 (the top line), and the two EEG channels (middle two lines), together with the spatial filtering result from analysis of all of the data (bottom line). The fact of an event is visible in all of the curves, but its occurrence is most clearly defined in the spatial filtering calculation. The clearer definition of the peak of the event results in a different conclusion as to the time at which the event apparently occurs, than would be reached from the measured data. This result suggests that spatial filtering can be used to determine not only the location within the brain, but also the time of occurrence of the event, more precisely than previously possible. Since events at one location within the brain propagate to other locations or trigger other events, both the exact location and time of the event are of significance.

Another approach to analyzing data using spatial filtering is to prepare a spatial map of intensity. The mapping is accomplished by using a single set of measured data, and then performing repeated spatial filtering calculations to determine the signal arising at each location of a raster of points within the brain. The results of the analysis are most readily visualized as a false color or gray scale image of the event in space at a moment in time. To do this, the signal magnitudes are associated with color ranges or a gray scale, and presented on a monitor or plotter. FIG. 8 is such a plot of data taken during an epileptic episode, presented in a five-color range. (Greater spatial resolution is attained with more colors.) The externally measured signals are seen to arise from two spatially distinct but apparently associated locations within the brain. This detailed structure of the event is not evident from visual inspection of the 37 channels of data, nor would it be determined from conventional dipole modeling of the event based upon the measured data. By making a series of plots such as FIG. 8, at a series of times before, during, and after the episode, the spatial and temporal evolution of the event within the brain can be determined and presented as a "movie". These results are of interest to the researcher to determine the origins and participating regions of an event as it evolves through time, and also to the doctor seeking a method of treatment.

The lead field synthesis or spatial filtering technique provides a valuable new approach for analyzing the magnetic signals (or electrical signals, with the appropriate sensors) generated within the human body, and particularly within the brain or the heart. The approach of the invention is used to analyze data collected from the sensors, to calculate the behavior of a source of interest while minimizing the effects of other sources within and also external to the brain. Although a particular embodiment of the invention has been described in detail for purposes of illustration, various modifications may be made without departing from the spirit and scope of the invention. Accordingly, the invention is not to be limited except as by the appended claims.

What is claimed is:

1. A process for sensing and evaluating signals emanating from a point within the brain of a subject, comprising the steps of:

providing an array of field sensors disposed external to a head of the subject at known locations;

the head of the subject emitting a field;

measuring a signal strength of the field at each of said sensors;

amplifying and filtering the signal strength measured at each of the sensors;

multiplying the amplified and filtered signal strength measured at each of said sensors times a weighting coefficient for that sensor to determine a virtual sensor contribution for each of said sensors, said weighting coefficient for each of said sensors being determined at least in part by the signal strengths detected by said array of sensors; and adding together the virtual sensor contribution of each of said sensors, to define a virtual sensor signal.

2. The process of claim 1, wherein each of said sensors is a magnetic field sensor.

3. The process of claim 1, wherein each of said sensors includes a superconducting quantum interference device.

4. The process of claim 1, wherein each of said sensors is an electric field sensor.

5. The process of claim 1, wherein the sensors are placed proximately to the head of the subject.

6. The process of claim 1, including, after the step of adding, the additional step of
correlating the virtual sensor signal with a physiological activity of the subject.

7. The process of claim 1, wherein the weighting coefficients $\vec{W}$ are calculated in matrix form as $$\vec{W} = [C_{ij}]^{-1} [\vec{G_T}] / [\vec{G_T}] \cdot [C_{ij}]^{-1} [\vec{G_T}]$$

where $C_{ij}$ is the covariance matrix of the measured signals of each of said sensors and $\vec{G_T}$ is the sensitivity matrix for each sensor, at a particular point.

8. The process of claim 1, including the additional step, after the step of adding, of
repeating the steps of multiplying and adding for a plurality of different points within the brain of the subject.

9. The process of claim 8, including the additional step, after the step of repeating, of
displaying the virtual sensor signals determined for the points in space on a spatial plot.

10. The process of claim 8, including the additional step, after the step of repeating, of
repeating the steps of measuring, multiplying, and adding for a signal determined at a different time.

11. A process for sensing and evaluating signals emanating from a body of a subject, comprising the steps of:
providing an array of electromagnetic field sensors disposed at locations external to a body of the subject;
measuring a signal strength at each sensor of the array of electromagnetic sensors;
amplifying and filtering the signal strength measured at each of the sensors; and
calculating a virtual sensor signal for the array, as a sum, over all of said sensors, of a product of a weighting coefficient for each sensor times the amplified and filtered signal measured for that sensor, the weighting coefficients being determined from measurements of the signal strengths of said array.

12. The process of claim 11, wherein the sensors are placed proximately to a chest of the subject.

13. The process of claim 11, wherein the weighting coefficients $\vec{W}$ are calculated in matrix form as $$\vec{W} = [C_{ij}]^{-1} [\vec{G_T}] / [\vec{G_T}] \cdot [C_{ij}]^{-1} [\vec{G_T}]$$

where $C_{ij}$ is the covariance matrix of the measured signals of each of said sensors and $\vec{G_T}$ is the sensitivity matrix for each sensor, at a particular point.

14. A process for sensing and evaluating magnetic signals emanating from a body of a subject, comprising the steps of:
providing an array of magnetic field sensors disposed external to the body of the subject at known locations;
measuring a signal strength at each of said sensors;
amplifying and filtering the signal strength measured at each of the sensors;
determining a weighting coefficient applicable to each of said sensors from the measurements made in said step of measuring;
multiplying the amplified and filtered signal strength measured by each of said sensors times the calculated weighting coefficient for that sensor to determine a virtual sensor contribution for each of said sensors; and
adding together said virtual sensor contribution of each of said sensors, to define a virtual sensor signal.

15. The process of claim 14, wherein the weighting coefficients $\vec{W}$ are calculated in matrix form as $$\vec{W} = [C_{ij}]^{-1} [\vec{G_T}] / [\vec{G_T}] \cdot [C_{ij}]^{-1} [\vec{G_T}]$$

where $C_{ij}$ is the covariance matrix of the measured signals of each of said sensors and $\vec{G_T}$ is the sensitivity matrix for each sensor, at a particular point.

16. The process of claim 14, including the additional step, after the step of adding, of
repeating the steps of multiplying and adding for a plurality of different points within the body of the subject.

17. The process of claim 16, including the additional step, after the step of repeating, of
displaying the virtual sensor signals determined for the plurality of different points on a spatial plot.

* * * * *